(12) United States Patent
McKay et al.

(10) Patent No.: US 10,167,268 B2
(45) Date of Patent: Jan. 1, 2019

(54) PROCESS FOR PURIFYING A CRUDE COMPOSITION OF DIALKYL ESTER OF 2,5-FURANDICARBOXYLIC ACID

(71) Applicant: Synvina C. V., Amsterdam (NL)

(72) Inventors: Benjamin McKay, Amsterdam (NL); Gerardus Johannes Maria Gruter, Amsterdam (NL); Johannes Maria Franciscus Sijben, Amsterdam (NL)

(73) Assignee: Synvina C.V., Amsterdam (NL)

( * ) Notice: Subject to any disclaimer, the term of this patent is extended or adjusted under 35 U.S.C. 154(b) by 0 days.

(21) Appl. No.: 15/525,415

(22) PCT Filed: Nov. 10, 2015

(86) PCT No.: PCT/NL2015/050782
§ 371 (c)(1),
(2) Date: May 9, 2017

(87) PCT Pub. No.: WO2016/076712
PCT Pub. Date: May 19, 2016

(65) Prior Publication Data
US 2018/0155306 A1    Jun. 7, 2018

(30) Foreign Application Priority Data
Nov. 10, 2014    (NL) ..................................... 2013766

(51) Int. Cl.
C07D 307/02    (2006.01)
C07D 307/68    (2006.01)

(52) U.S. Cl.
CPC .................................. C07D 307/68 (2013.01)

(58) Field of Classification Search
CPC ................................................... C07D 307/68
(Continued)

(56) References Cited

U.S. PATENT DOCUMENTS 4,683,034 A    7/1987    Bader et al.
5,542,372 A    8/1996    Sun et al.
(Continued)

FOREIGN PATENT DOCUMENTS

EP    1380566 A1    1/2004
EP    2486027 B1    6/2014
(Continued)

OTHER PUBLICATIONS

Stepanski et al, Reinigung von Produkten aus nachwachwachsenden Rohstoffen mit fraktionierter Kristallisation, Sulzer Chemtech AG, Feb. 2008, p. 1-34 (Year: 2008).*
(Continued)

*Primary Examiner* — Taylor V Oh
(74) *Attorney, Agent, or Firm* — Hoffmann & Baron, LLP (57) ABSTRACT

An ester composition including at least 90% wt of the dialkyi ester of 2,5-furandicarboxylic acid as starting dialkyi ester concentration and up to 5% wt of the monoalkyi ester of 2,5-furandicarboxylic acid as starting monoalkyi ester concentration, the percentages being based on the weight of the ester composition, is purified in a process which includes subjecting the ester composition to melt crystallization to yield a purified dialkyi ester composition containing a dialkyi ester concentration higher than the starting dialkyi ester concentration and a melt residue containing a monoalkyi ester concentration higher than the starting monoalkyi ester concentration. From the melt residue a purified monoalkyi ester composition and a contaminants-rich residue can be prepared via melt crystallization. The purified dialkyi ester composition and/or the purified monoalkyi ester composition can be hydrolyzed to yield purified 2,5-furandicarboxylic acid.

18 Claims, 1 Drawing Sheet

(58) Field of Classification Search
USPC .......................................................... 549/485
See application file for complete search history.

(56) References Cited

U.S. PATENT DOCUMENTS

2011/0282020 A1    11/2011  Sipos
2013/0345448 A1*   12/2013  Shaikh ................. C07D 307/68
                                                        549/485

FOREIGN PATENT DOCUMENTS

WO    2013/062408 A1    5/2013
WO    2013/191942 A1    12/2013

OTHER PUBLICATIONS

Wikipedia, 2,5-furandicarboxylic acid, Mar. 2013, p. 1-3. (Year: 2013).*

* cited by examiner

PROCESS FOR PURIFYING A CRUDE COMPOSITION OF DIALKYL ESTER OF 2,5-FURANDICARBOXYLIC ACID

CROSS-REFERENCE TO RELATED APPLICATIONS

This application is the National Stage of International Application No. PCT/NL2015/050782 filed Nov. 10, 2015, which claims the benefit of Netherlands Application No. NL 2013766, filed Nov. 10, 2014, the contents of which is incorporated by reference herein.

FIELD OF THE INVENTION

The present invention relates to a process for purifying a crude ester composition comprising a dialkyl ester and a monoalkyl ester of 2,5-furandicarboxylic acid.

BACKGROUND OF THE INVENTION

Dialkyl esters of 2,5-furandicarboxylic acid (2,5-FDCA) have found use as monomers in the preparation of bio-based polyesters. The preparation of such polyesters has been disclosed in e.g. US 2011/0282020 and WO 2013/062408. The preparation comprises the polycondensation reaction of an alkylene diol with the dialkyl ester of 2,5-FDCA. Alternatively, the acid can be used as monomer. When the acid is used as monomer it still can be convenient to prepare the dialkyl ester first and subject the dialkyl ester obtained to saponification, since the purification of crude 2,5-FDCA appears to be more cumbersome than the purification of the esters. The resulting polyester can be used as alternative for polyethylene terephthalate (PET), as stated in WO 2013/062408.

The preparation of the dialkyl ester of 2,5-FDCA is known in the art. In this context reference is made to e.g. EP2486027, describing a process wherein from a carbohydrate an ether of 5-hydroxymethylfurfural is prepared, which ether is subsequently oxidized to a product containing 2,5-FDCA and esters thereof. The product may be further esterified to yield an ester composition comprising the dialkyl ester of 2,5-FDCA and the monoalkyl ester thereof. It was found that the ester composition also typically contains some contaminants that cause coloration of the resulting polymer.

In order to enable the manufacture of transparent, colorless polyesters it is therefore desirable to purify the ester composition. It is known that the purification of the corresponding monomers for the preparation of PET can be accomplished by the distillation or crystallization of a crude ester composition of dimethyl terephthalate. In U.S. Pat. No. 4,040,793 it is disclosed that crystallization and recrystallization involve considerable cost since each recrystallization step requires four steps: the creation of a genuine solution, the crystallization as such, then the separation of the crystallized material and finally the washing of the crystals obtained. In U.S. Pat. Nos. 4,683,034 and 5,542,372 processes for the purification of dimethyl terephthalate are described wherein dimethyl terephthalate is separated from the dimethyl esters of isophthalic acid and orthophthalic acid by means of a combination of evaporation, crystallization and melt crystallization. These patent documents are silent about coloration-causing compounds.

Also as to the process according to EP 1380566 it was proposed that for the purification of dimethyl terephthalate melt crystallization is used. However, it appeared that melt crystallization alone is insufficient to obtain a sufficiently pure product. EP 1380566 therefore discloses a process that includes the esterification of the oxidation product of p-xylene and methyl p-toluate to yield a crude ester product, a distillation step to separate a light fraction from the crude ester product, a flash distillation to separate heavy, coloration-causing compounds from the crude ester product and at least two melt crystallization steps to obtain purified dimethyl terephthalate from the crude ester product. Between the two melt crystallization steps, the crystallization product of the first melt crystallization is again treated in an additional distillation column to remove coloration-causing compounds therefrom before being subjected to the second melt crystallization. This process shows the difficulty of the removal of coloration-causing compounds.

SUMMARY OF THE INVENTION

It has now surprisingly been found that for a crude ester composition of 2,5-FDCA there is no need for additional distillation steps to remove coloration-causing compounds if the melt crystallization is conducted such that the monoalkyl ester of 2,5-FDCA is being separated from the dialkyl ester thereof. Such a separation can be accomplished when the crude ester composition comprises at least 90% wt of the dialkyl ester and up to about 5% wt of the monoalkyl ester based on the weight of the composition. It is further surprising that when the crude ester composition comprises higher contents of the monoalkyl ester, purification of such ester compositions by melt crystallization is difficult to accomplish and can only be achieved at very low yields.

Accordingly, the present invention provides a process for purifying an ester composition comprising at least 90% wt of the dialkyl ester of 2,5-furandicarboxylic acid as starting dialkyl ester concentration, and up to 5% wt of the monoalkyl ester of 2,5-furandicarboxylic acid as starting monoalkyl ester concentration, the percentages being based on the weight of the ester composition, which process comprises subjecting the ester composition to melt crystallization to yield a purified dialkyl ester composition containing a dialkyl concentration higher than the starting dialkyl ester concentration and a melt residue containing a monoalkyl ester concentration higher than the starting monoalkyl ester concentration. Due to the high concentration of the dialkyl ester and the low amount of the monoalkyl ester the melt crystallization process allows for the separation of the dialkyl ester from the monoalkyl ester together with any contaminants that are contained in the ester composition.

The ester composition may contain up to about 10% wt of contaminants, based on the weight of the ester composition, preferably at most 5% wt. Contaminants may have been formed during preceding reactions. As indicated above, the ester composition may be the product from a range of reactions, including the dehydration of carbohydrates to form 5-hydroxymethyl furfural, or ethers or esters thereof. The obtained products of the dehydration may be oxidized to 2,5-FDCA or derivatives thereof by an oxidant over an oxidation catalyst, typically a catalyst containing cobalt and manganese. The oxidation product may then be further esterified with an alkanol. During these reactions, in particular during the oxidation reaction, impurities and/or by-products (hereinafter together; contaminants, i.e. compounds other than the dialkyl ester and monoalkyl ester of FDCA) may be formed, in addition to the dialkyl ester and monoalkyl ester of 2,5-FDCA. Such contaminants may include the esterification starting material 2,5-FDCA and one or more compounds selected from the group consisting of 5-formyl-furan-2-carboxylic acid (FFCA), an alkyl ester of FFCA, and coloration-causing compounds. The presence of FFCA and derivatives thereof is undesired since it causes the termination of any subsequent polycondensation reaction with a diol.

It has been found that the melt crystallization of a crude ester composition of the dialkyl ester of 2,5-FDCA, wherein the starting concentration of monoalkyl ester of 2,5-FDCA is about 10% wt or more, does not yield a purified dialkyl ester composition wherein the content of the dialkyl ester has been increased to levels significantly above 90% wt. It was found that the highest purity of the dialkyl ester of 2,5-FDCA that could be obtained in this way was in the range of about 90 to 92% wt. It is therefore surprising that when the level of monoalkyl ester is below 5% wt and the level of the dialkyl ester is above 90% wt, not only a purified dialkyl ester product with a further reduced level of the monoalkyl ester is obtained, but also the contaminants, including coloration-causing compounds, are separated together with the monoalkyl ester. Without wishing to be bound by a theory, it is believed that the monoalkyl and dialkyl esters of 2,5-FDCA form a eutectic wherein the amount of monoalkyl ester is in the region of 8 to 10% wt. When the composition of a mixture of these esters is similar to the eutectic composition the separation of such a mixture into the pure components by melt crystallization becomes virtually impossible. The process according to the present invention allows the provision of a purified dialkyl ester composition wherein the dialkyl ester concentration may be as high as at least 98% wt, preferably, at least 99% wt, and more preferably at least 99.5% wt. The concentration of monoalkyl ester can be lowered to a level of at most 1000 ppm, preferably at most 800 ppm.

Melt crystallization is a technique that is known in the art and has been described in e.g. U.S. Pat. Nos. 5,542,372, 4,683,034 and EP 1380566. The technique comprises the provision of a molten feed that is contacted with a cool surface. Upon such contact crystallization of the molten feed starts. Melt crystallization is based on the principle that when an impure molten material is cooled to below its freezing point and further heat is removed, some of the material will solidify. Whereas the solidified material tends to be pure, the impurities concentrate in the melt. Purified material is recovered by separating the solidified material from the melt and, optionally, by re-melting it. Melt crystallization is suitably carried out as layer crystallization or suspension melt crystallization. In a layer crystallization process the solid material to be formed is created on the cooled surface. In suspension melt crystallization crystals are created on the cooled surfaces of a heat exchanger. The crystals are scraped from the surfaces and are allowed to grow in a stirred growth vessel. After maturing in this vessel to a sufficient size the crystals are transported to a piston type wash column where they are separated from the melt residue.

Layer crystallization can be accomplished as static crystallization or as falling film crystallization. In both processes the crystallization takes place on cooled surfaces. In static crystallization the crystallization takes place on cooled plates immersed in a stagnant melt composition. Preferably, the present process is conducted as falling film crystallization. In such a process the melt flows down along the walls of tubes as cooled surfaces, e.g. the inside walls of the tubes, whereas a cooling medium is distributed along the other side of the tubes, e.g. along the outside walls. For re-melting the cooling medium can be replaced by a heating medium. Hence, the process according to the present invention is suitably conducted in a static or a falling film and/or a suspension melt crystallization equipment, wherein the use of static crystallization equipment or falling film crystallization equipment is preferred.

In the present process the dialkyl ester of 2,5-FDCA crystallizes from the ester composition and forms a virtually pure layer of solid material on the cooled surface, e.g. the tubes of a falling film crystallizer. The monoalkyl ester, but also contaminants such as 5-formyl-furan-2-carboxylic acid, the alkyl ester or esters thereof, 2,5-FDCA, and the coloration-causing compounds, are concentrated in the remaining melt. Therefore, the melt crystallization is suitably conducted in a falling film equipment, wherein the molten ester composition is passed along the walls of cooling tubes to effect crystallization of the dialkyl ester of 2,5-FDCA on the walls of the cooling tubes.

In order to enhance the purity it has been found that it is advantageous to slightly re-heat the solid material before it is re-melted for recovery. The slight re-heating means that the temperature is brought to a temperature that does not exceed the melting point of the pure dialkyl ester of 2,5-FDCA. At the slight re-heating lower-melting components re-melt first and can be collected as a separate fraction of low-melting components. The fraction will contain also the dialkyl ester in addition to any low-melting component. This fraction may be combined with the remaining melt, but it is also possible to collect it as a separate fraction and treat it separately from the remaining melt. Accordingly, the present process is suitably conducted such that, after the crystallization of the dialkyl ester of 2,5-FDCA on the cooled surfaces, the cooled surfaces are re-heated to a temperature below the melting point of the dialkyl ester of 2,5-FDCA, to effect the melting of low-melting components. This technique is known as "sweating". The fraction of low-melting components that may be recovered in this way is therefore also known as the "sweat". The molten low-melting components may therefore be obtained as sweat, in addition to the purified dialkyl ester composition and the melt residue.

For a number of applications of the dialkyl ester of 2,5-FDCA the purity thereof is of paramount importance. Therefore, it may be advantageous to conduct the melt crystallization in several steps, wherein the melt crystallization is repeated one or more times to enhance the purity of the eventual product. Thereto the process according to the present invention may be conducted such that the ester composition in a first step is subjected to melt crystallization yielding a first purified diester composition, a first melt residue and optionally a first sweat, wherein the first purified diester composition is subjected to a subsequent melt crystallization step yielding a subsequent purified diester composition and subsequent melt residue and optionally a subsequent sweat, wherein the subsequent purified diester composition may be obtained as desired product. The procedure may be repeated several times. Suitably, the number of repetitions may be from 2 to 7, preferably, from 2 to 4. When more than one step is applied in the melt crystallization process, there is no necessity to employ multiple melt crystallizers. The steps may be conducted in sequence in a single melt crystallizer.

In such a procedure, it is advantageous to combine the subsequent melt residue, and optionally sweat, with a further portion of the ester composition. The subsequent melt residue may be combined with the first ester residue, and subjected to a separate melt crystallization step. The purified product of this separate melt crystallization step can be combined with a further portion of the ester composition and optionally with a subsequent melt residue.

The conditions at which the melt crystallization is conducted are determined by the compound to be purified, in particular it depends on the alkyl group in the dialkyl ester moieties. Typically the ester composition comprises the dialkyl ester wherein the alkyl group comprises 1 to 6, preferably 1 to 4 carbon atoms. It is especially preferred to carry out the process of the present invention on the dimethyl ester of 2,5-FDCA. Typically, the ester composition being subjected to the melt crystallization has a temperature in the range of 110 to 150° C. The cooled surfaces typically have temperature well below the melting point of the dialkyl ester of 2,5-FDCA. Such temperatures are suitably in the range of 80 to 110° C. This temperature is controlled by using the temperature of the heat transfer medium (cooling medium) that is used in the melt crystallization. Evidently, when the solid material is to be re-melted, the temperature of the surfaces and of the solid material is enhanced to above the melting point of the dialkyl ester of 2,5-FDCA. Typically the temperature is then in the range of 110 to 150° C. When a sweat step is envisaged, the temperature of the surfaces and solid material is re-heated to a temperature up to the melting point of the dialkyl ester. Suitably, the temperature of the heat transfer medium is then in the range from 85 to 118° C. It is evident that these conditions are more favourable than the conditions that are to be applied when the purification of the ester composition is to be accomplished by distillation. Moreover, since purification by distillation is more difficult to achieve at economic scale than by melt crystallization, the present process provides significant technical and economic advantages over conventional distillation purification.

The melt residue that is being recovered contains an enhanced concentration of the monoalkyl ester of 2,5-FDCA. The composition also contains a significant level of the dialkyl ester. The composition of the melt residue may be similar to the eutectic composition as explained above. Therefore, it has been difficult to recover the dialkyl ester from compositions containing such an enhanced level of the monoalkyl ester. However, if the composition is changed to a composition containing a monoalkyl ester concentration well beyond the monoalkyl ester concentration at the eutectic point, the separation of the monoalkyl ester from the melt residue may be accomplished. One can therefore add monoalkyl ester to the melt residue to increase the content of the monoalkyl ester to the desired value. However, for such addition one needs to have an additional amount of monoalkyl ester of FDCA. Therefore, in order to recover valuable products from the melt residue, it is found to be advantageous to convert the melt residue into a monoalkyl ester-rich intermediate product, containing a monoalkyl ester concentration beyond that at the eutectic point, such as a concentration of at least 10% wt product, based on the weight of the intermediate product, and, optionally, subject the intermediate product to melt crystallization to obtain a purified monoalkyl ester composition and a contaminants-rich residue. The conversion of the melt residue into the monoalkyl ester-rich intermediate product is aimed at the reaction of the dialkyl ester to the corresponding monoalkyl ester. Generally, three ways to achieve this conversion are available to the skilled person. The first way is the transesterification of the dialkyl ester with 2,5-FDCA. In this procedure 2,5-FDCA is added to the melt residue, typically at temperatures above 200° C., e.g. from 200 to 300° C. Preferably, no transesterification catalyst is added in order to avoid the presence of additional contaminants.

A second manner to obtain the intermediate product is to subject the melt residue to partial hydrolysis. Since the hydrolysis is catalysed by acidic moieties, the presence of the acid groups of the monoalkyl ester catalyzes the hydrolysis. Thus the partial hydrolysis can be effected by the insertion of water, e.g. in the form of steam, to the melt residue. By ascertaining that the amount of water does not exceed the amount necessary for the partial hydrolysis, the yield of the monoalkyl ester can be optimized. In this way the intermediate product has a high level of monoalkyl ester, whilst an excess formation of 2,5-FDCA and also the saponification of any other esters are substantially avoided. The present process therefore is preferably carried out such that the melt residue is subjected to partial hydrolysis. Conditions for the partial hydrolysis can be selected from wide ranges, which include a temperature of 100 to 200° C. and a pressure of 1 to 30 bar, preferably, a temperature of 120 to 180° C. and a pressure of 2 to 15 bar.

A third way to arrive at a monoalkyl ester-rich intermediate product from the melt residue is by subjecting the melt residue to evaporation, such as falling film evaporation. By evaporation the relatively low-boiling dialkyl ester of 2,5-FDCA is vaporized and may be recovered as product or be recycled to the melt crystallization. The remaining liquid of the evaporation consists of monoalkyl and dialkyl esters of 2,5-FDCA and some contaminants, such as coloration-causing compounds. By evaporation the monoalkyl ester concentration in the remaining liquid is suitably brought to a value of at least 10% wt, based on the remaining liquid. The remaining liquid is recovered as an intermediate product.

Advantageously, the intermediate product that is obtained in one of the methods described above is subsequently subjected to melt crystallization. The melt crystallization of the intermediate product may be carried out as a falling film, static or suspension melt crystallization. Falling film crystallization is preferred.

As in the case of the initial ester composition, the temperature and other conditions of the melt crystallization of the monoalkyl ester-rich intermediate product can be adapted in accordance with the alkyl group in the intermediate product. It is also preferred to carry out the melt crystallization such that a sweat product is obtained. The melt crystallization of this intermediate product may also comprise several steps, wherein the sweat product of a step may be added to a portion of the intermediate product of a subsequent step. Typically, the melt crystallization of the intermediate product is conducted such that the monoalkyl ester-rich intermediate product has a temperature in the range of 160 to 250° C. The cooled surfaces typically have temperature well below the melting point of the monoalkyl ester and may be in the same range as for the initial ester composition or somewhat higher, such as 140 to 200° C. Evidently, when the solid material is to be re-melted, the temperature of the surfaces and of the solid material is enhanced to above the melting point of the monoalkyl ester of 2,5-FDCA. Typically the temperature is then in the range of 160 to 250° C. When a sweat step is envisaged, the temperature of the surfaces and solid material is re-heated to a temperature up to the melting point of the monoalkyl ester. Suitably, the temperature is in such a sweat step in the range from 160 to 250° C.

The product of the process according to the present invention includes the dialkyl ester of 2,5-FDCA. When the melt residue is treated to form a monoalkyl ester-rich intermediate product that is also purified, the product of the process according to the present invention also comprises purified monoalkyl ester of 2,5-FDCA. When the desired product is the dialkyl ester, the monoalkyl ester may be further esterified by the reaction of the monoalkyl ester with additional alkanol. Such a reaction may be accomplished in the presence of an acid catalyst, but since the monoalkyl ester already comprises an acidic moiety the addition of an additional acidic catalyst is not necessary.

However, since it is difficult to obtain 2,5-FDCA in sufficient purity, the process according to the present invention provides an excellent and convenient route to a suitable starting material, viz. the dialkyl ester and, optionally, the monoalkyl ester, in high purity which can be easily converted into 2,5-FDCA.

Accordingly, the present invention also provides a process for the preparation of 2,5-FDCA from an ester composition comprising at least 90% wt of the dialkyl ester of 2,5-FDCA as starting dialkyl ester concentration and up to 5% wt of the monoalkyl ester of 2,5-FDCA as starting monoalkyl ester concentration, the percentages being based on the weight of the ester composition, which process comprises:

subjecting the ester composition to melt crystallization to yield a purified dialkyl ester composition containing a dialkyl ester concentration higher than the starting dialkyl ester concentration and a melt residue containing a monoalkyl ester concentration higher than the starting monoalkyl ester concentration; and hydrolysing the purified dialkyl ester composition to yield purified 2,5-FDCA.

As explained above, the process according to the present invention may also result in the production of a purified monoalkyl ester composition. This purified monoalkyl ester composition will also result in yielding the dicarboxylic acid itself when hydrolysed. The hydrolysis product is therefore the same as that of the hydrolysis of the dialkyl ester. Hence it is advantageous to hydrolyse the purified monoalkyl ester product. Thus, the process also preferably comprises subjecting the melt residue to conversion into a monoalkyl ester-rich intermediate product containing a monoalkyl ester concentration of at least 10% wt product, based on the weight of the intermediate product;

subjecting the monoalkyl ester-rich intermediate product to melt crystallization to yield a purified monoalkyl ester composition; and hydrolysing the purified monoalkyl ester composition to yield purified 2,5-FDCA.

The conversion of the melt residue into the monoalkyl ester-rich intermediate product; can suitably be effected by transesterification or partial hydrolysis or evaporation as described above, the latter two methods being preferred.

Hydrolysis in general is carried out in the presence of an acidic or alkaline catalyst. Since the monoalkyl ester already possesses an acidic moiety and thereby renders it unnecessary to add any additional catalyst, it is preferred to combine the purified dialkyl ester composition and the purified monoalkyl ester composition, and hydrolyse the obtained combination simultaneously.

The ester composition that is being subjected to melt crystallization can be obtained in a variety of ways. In a very suitable manner it has been obtained in a process, comprising:

contacting a vaporous stream of an alkanol countercurrently with a liquid starting material comprising 2,5-FDCA in a reaction zone to conduct an esterification reaction;

withdrawing a reaction vapor comprising the alkanol and water from the reaction zone; and discharging a liquid phase comprising at least the dialkyl ester of 2,5-FDCA, from the bottom part of the reaction zone, to obtain the ester composition comprising the dialkyl ester of 2,5-FDCA.

The alkanol in the reaction zone suitably comprises 1 to 4 carbon atoms, and is preferably methanol. The reaction zone advantageously comprises a reactive stripping column. It suitably comprises reactor internals and/or a packing, preferably internals, more preferably sieve plates.

The reaction vapor comprising the alkanol and water may be separated into an alkanol fraction and a water fraction, e.g. by distillation. When this is done, the alkanol fraction can be recycled to the reaction zone. Also a portion of the liquid phase may be recycled to the reaction zone. This may be accomplished by splitting the liquid phase from the esterification reaction and recycle one portion to the reaction zone. Optionally, a minor portion thereof may be discharged as a bleed stream in order to avoid the buildup of an excessive amount of contaminants. It is particularly preferred to separate the liquid phase obtained in the esterification zone into a first fraction rich in the monoalkyl ester of 2,5-FDCA and a second fraction rich in the dialkyl ester of 2,5-FDCA. The second fraction is subsequently used as the ester composition and subjected to the melt crystallization according to the present invention. By this separation it is ascertained that the portion of the monoalkyl ester in the ester composition is well below the level of 5% wt, so that the melt crystallization achieves its advantageous results.

The esterification in the reaction zone may be conducted at a reaction temperature in the range of 150 to 300° C., and a pressure of 5 to 25 bar. Although the melt crystallization is a batch process, the preparation of the ester composition by means of the above-described esterification may be conducted in a continuous process.

BRIEF DESCRIPTION OF THE DRAWINGS

The process according to the present invention will be further elucidated by means of the following Figures.

DETAILED DESCRIPTION OF THE INVENTION

Figure 1:
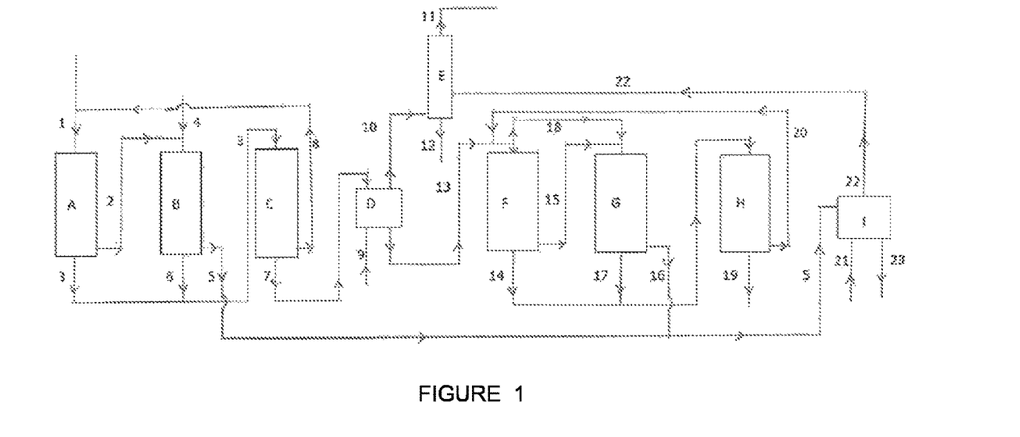
FIG. 1 shows a simplified flow scheme for an embodiment of the present process showing the integration of several melt crystallization methods.

A crude ester composition, comprising more than 90% wt, based on the ester composition, of the dialkyl ester of 2,5-FDCA, e.g. dimethyl-2,5-furandicarboxylate, is passed via a line 1 to a melt crystallizer A. Melt crystallizer A may conveniently be a falling film melt crystallizer comprising a tube bundle wherein the crude ester composition is passed along the inner wall of the tubes and a heat transfer medium is passed on the outer side of the walls. The ester composition is passed along the cooled surfaces of the tubes, thereby solidifying. The melt residue that does not solidify on the inner walls of the tubes is withdrawn via a line 3. Via the same line 3 the sweat that is obtained by slightly re-heating the solidified material, is combined with the melt residue. After re-melting of the solidified material the re-molten fluid is withdrawn from the melt crystallizer A via a line 2 and combined with another fraction of the crude ester composition, supplied via a line 4. The combined re-molten material and the fraction of crude ester composition is passed to a second melt crystallizer B, where they are treated in a similar way as the crude ester composition of the line 1. The melt residue and sweat of the melt crystallizer B are withdrawn from this crystallizer and combined with the melt residue and sweat in the line 3. The purified dialkyl ester composition, i.e. virtually pure dimethyl-2,5-furandicarboxylate, is withdrawn from the melt crystallizer B via a line 5.

The combined melt residues and sweats in the line 3 are passed to a third melt crystallizer C, wherein the combined material in the line 3 is subjected to melt crystallization yielding a fluid melt residue and sweat in a line 7 and a re-molten material in a line 8. Since the line 8 contains material with a significant amount of dialkyl ester, the material in line 8 is recycled to one of the earlier melt crystallizers, in this case to the melt crystallizer A, where it is combined with the crude ester composition in the line 1.

It is observed that melt crystallization is a batch process. Whereas in the figure the melt crystallizers are shown as three separate pieces of equipment, it is clear that the number of crystallizers may be smaller or larger. The figure shows just a mode of operation indicating a possible sequence of process steps.

The melt residue in the line 7 may be discarded. However, in a preferred embodiment of the present process, the melt residue in the line 7 contains a significant amount of the monoalkyl ester, such as the monomethyl ester of 2,5-FDCA. In order to recover this valuable product the melt residue is passed via the line 7 to a hydrolysis reactor D. In the hydrolysis reactor D steam, supplied via a line 9, is added to the reaction mixture. In the hydrolysis reactor D the dialkyl ester is converted into the monoalkyl ester. With that reaction also alkanol, such as methanol is yielded. The alkanol, such as methanol, is withdrawn from the reactor D via a line 10. The monoalkyl ester is obtained as a monoalkyl ester-rich intermediate product which is withdrawn from the reactor D via a line 13. It is then passed to a melt crystallizer F yielding a first purified monoalkyl ester product via a line 15 and a first melt residue and sweat via a line 14. The first purified monoalkyl ester product is suitably passed to a further melt crystallizer G, where it is, optionally, combined with another portion of the intermediate product from line 13, supplied via a line 18. The melt crystallizer G yields a purified monoalkyl ester composition that is withdrawn via a line 16, and a further melt residue and sweat that is withdrawn via a line 17. The latter melt residue and sweat from the line 17 is added to the melt residue and sweat in the line 14, and the combined contents in the line 14 is passed to a melt crystallizer H. The feed of the melt crystallizer G is divided into a contaminants-rich melt residue, optionally with some material from a sweat step, withdrawn via a line 19, and a fraction that is solidified and re-molten via a line 20. Since line 20 contains a significant amount of the desired monoalkyl ester, the fraction is recycled to a previous melt crystallizer, in this case the melt crystallizer F where it is combined with the intermediate product from the line 13.

The purified dialkyl ester product from the line 5 and the purified monoalkyl ester product from the line 16 may be recovered as separate end-products. However, if the desired product is purified 2,5-FDCA, the product from the line 16 may be added to that of the line 5 and the combined products may be passed via the line 5 to a hydrolysis reactor I. In this reactor steam is added to the reaction mixture via a line 21, wherein the amount of water is sufficient to hydrolyse all ester groups. In the hydrolysis reaction alkanol, such as methanol, is liberated, which is withdrawn via a line 22. In order to recover the alkanol, the alkanol may be passed via the line 22 to a distillation column E. In addition to the alkanol from the line 22, the distillation column E may also be supplied with the alkanol from the line 10, from the hydrolysis reactor D. The distillation column E yields an alkanol stream 11. This alkanol can be recovered and may be used elsewhere in the production process of the crude ester composition. Any heavier by-products can be discharged via a line 12.

The eventual product, i.e. purified 2,5-FDCA, is obtained in the hydrolysis reactor I and recovered via a line 23.

Figure 2:
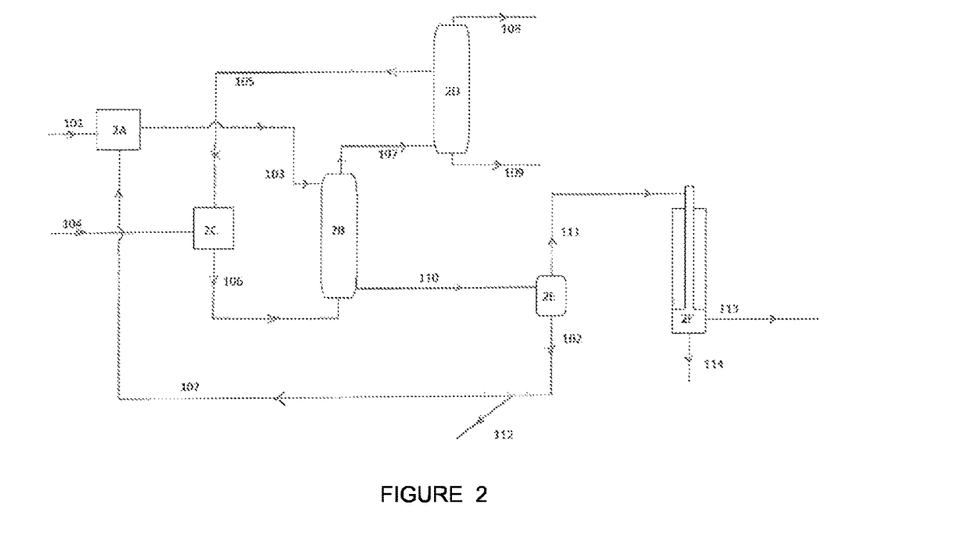
FIG. 2 shows a different embodiment, wherein a production process of the crude ester composition is schematically shown, which composition is subsequently purified by melt crystallization.

Referring to FIG. 2, this figure shows a stream comprising 2,5-FDCA that is supplied via a line 101 to a mixing zone 2A. The stream may comprise 2,5-FDCA and in addition may also contain the monoester of 2,5-FDCA, e.g. the monomethyl ester. In the mixing zone 2A the 2,5-FDCA or mixture of 2,5-FDCA and monoester thereof is combined with a liquid stream comprising the dialkyl-2,5-furandicarboxylate that is provided via a line 102. The liquid stream in the line 102 may also comprise an amount of monoalkyl ester of 2,5-FDCA. The combined liquid stream is withdrawn from the mixing zone 2A via a line 103 and passed to a reaction zone 2B. Reaction zone 2B may be in the form of a reactive stripping column. The combined liquid stream in the line 103 is then introduced into the upper part of the reactive stripping column 2B. The reactive stripping column 2B may be provided with sieve plates that contain holes to allow the flow of liquid from the top to the bottom, and the flow of vapor from the bottom to the top, whereas backmixing is reduced. The vapor in the reactive stripping column 2B is provided by a stream of an alkanol that is introduced into the lower part of the stripping column 2B via a line 106. In the stripping column an esterification reaction between the 2,5-FDCA and alkanol takes place while the alkanol is counter-currently contacted with the 2,5-FDCA. Any water that is formed during the esterification is withdrawn as water vapor together with the alkanol vapor. Thereby the equilibrium of the esterification reaction is shifted and the esterification reaction is allowed to run to virtual completion. The reaction vapor comprising the alkanol and water is withdrawn from the top of the reactive stripping column and passed to a distillation column 2D through a line 107, to allow for the separation of the alkanol and water. During distillation in the distillation column 2D the water fraction is usually recovered as the bottom fraction and thus withdrawn from the bottom of the distillation column 2D via line 109. Water thus recovered is usually discharged.

During the residence of the alkanol in the reactive stripping column 2B, some by-products may have been formed, e.g. the dialkyl ether through the etherification of the alkanol in the acid environment of the column 2B. The dialkyl ether is then also separated from the alkanol and, when the ether is the fraction with the lower boiling point, it will be withdrawn from the distillation column 2D via a line 108, whereas the alkanol is recovered and withdrawn from the distillation column 2D via a line 105.

The alkanol fraction in the line 105 is passed to a combination zone 2C, where it is combined with fresh make-up alkanol, provided via a line 104. The combined stream of alkanol is passed via the line 106 to the reactive stripping column 2B. In this way the alkanol is effectively recycled.

The dialkyl-2,5-furandicarboxylate that is formed in the reactive stripping column 2B is discharged as a liquid phase from the bottom part of the reactive stripping column 2B via a line 110. In the line 110 the liquid phase containing the dialkyl ester is passed to a separation zone 2E. In the separation zone 2E the liquid phase is separated into a recycle stream that is passed via the line 102 to the mixing zone 2A, and into a crude ester composition rich in the dialkyl-2,5-furandicarboxylate that is withdrawn via a line 111. The liquid phase from the reactive stripping column 2B may comprise a minor amount of heavy by-products in the form of high-boiling contaminants that may have been formed during the production of 2,5-FDCA. In such a case it is effective to provide for a bleed stream. Such a bleed stream may be obtained by splitting the liquid phase of the line 102 into a minor stream that is discharged via line 112.

The separation zone 2E is suitably an evaporation zone which results in a product stream rich in dialkyl ester and a recycle stream containing at least the major part of the monoalkyl ester that is contained in the liquid phase from reactive stripping column 2B.

The crude ester composition, rich in the dialkyl ester of 2,5-FDCA, in the line 111 is passed to a melt crystallizer 2F, from which purified dialkyl ester is recovered via a line 113 and melt residue, which contains the major part of any monoalkyl ester, present in the crude ester composition, that is withdrawn via a line 114.

In FIG. 2 only one melt crystallizer has been shown. It is evident that more than one crystallizer may be used. It is further evident that the melt residue that is withdrawn via the line 114 may be recycled to the same or another melt crystallizer to obtain as much dialkyl ester product as feasible.

The invention is further illustrated by means of the following Examples.

EXAMPLE 1

A crude composition comprising dimethyl 2,5-furandicarboxylate and the monomethyl ester of 2,5-FDCA was subjected to a melt crystallization step. The composition contained about 2.1% wt of the monomethyl ester of 2,5-FDCA and about 800 ppmw of other impurities, the balance being dimethyl-2,5-furandicarboxylate. These percentages were based on the weight of the composition. It had a freezing point of 108.40° C.

The melt crystallization was performed according to the following procedure. Vertical plates, heated or cooled by internal circulation of a heat transfer medium were suspended in a box with the molten crude composition. By slowly cooling of the heat transfer medium to below the freezing point of the crude composition, crystals started to grow onto the plates. When a predetermined layer of crystals had developed, the remaining molten material, into which contaminants had concentrated, was drained and collected as melt residue. This was done at different temperatures of the heat transfer medium. The respective fractions were collected. Subsequently, the remaining layer of crystallized material was ultimately melted and recovered as product.

The freezing points of the fractions recovered were determined. As the freezing point of a solid composition is lowered as the composition is less pure, the level of the freezing point indicates the level of purity obtained. Table 1 below indicates the temperature of the heat transfer medium (HTM) at the crystallization stage, sweating stages and the ultimate melting stage, the amount of each fraction, indicated as percentage of the composition that was fed into the melt crystallizer and the freezing point of that fraction.

TABLE 1

| Fraction No. | HTM, ° C. | Amount, % | Freezing point, ° C. |
|---|---|---|---|
| 1-1 | 104 | 8.9 | 104.35 |
| 1-2 | 108 | 7.4 | 105.16 |

TABLE 1-continued

| Fraction No. | HTM, ° C. | Amount, % | Freezing point, ° C. |
|---|---|---|---|
| 1-3 | 112 | 11.6 | 108.02 |
| 1-4 | 130 | 71.9 | 109.15 |

Fraction 1-1 was the melt residue. Fractions 1-2 and 1-3 were sweat fractions. Fraction 1-4 was recovered as product. It has the highest freezing point, indicating its increased purity. The composition of Fraction 1-4 was analyzed and it was found to contain 0.6% wt of the monomethyl ester of 2,5-FDCA, based on the weight of Fraction 1-4. The level of other impurities, including coloration-causing compounds, was 42 ppmw. The balance of the fraction was dimethyl-2,5-furandicarboxylate.

The example shows that melt crystallization is an excellent method for purifying the crude ester composition.

EXAMPLE 2

To show the suitability of sweat fraction for the recycling thereof, Fraction 1-3 was mixed with a portion of the original crude composition that was also used in Example 1. The amount of Fraction 1-3 was about 11% wt, based on the resulting mixture. The mixture was subjected to melt crystallization, following in general the procedure as outlined in Example 1, but only one fraction was collected as sweat fraction. The amounts indicated are shown as percentages of the composition that was fed into the melt crystallizer. The results are shown in Table 2 below.

TABLE 2

| Fraction No. | HTM, ° C. | Amount, % | Freezing point, ° C. |
|---|---|---|---|
| 2-1 | 107 | 27.4 | 106.03 |
| 2-2 | 112 | 11.8 | 108.44 |
| 2-3 | 130 | 60.7 | 109.36 |

Fraction 2-1 is the melt residue, and Fraction 2-2 is a sweat fraction. Fraction 2-3 is the product. By allowing a larger portion of the feed to be discharged as sweat fraction, the purity of the fraction that is recovered as product, i.e. Fraction 2-3, can be further increased, as shown by the higher freezing point. Also the suitability of several fractions for recycling is shown in this example.

Fraction 2-3 was further purified by subjecting this fraction again to melt crystallization. The Fraction 2-3 was separated into a melt residue (Fraction 2-4), a sweat fraction (Fraction 2-5) and a final product fraction (Fraction 2-6). Table 3 shows the HTM temperature, the amounts of the fractions, based on the weight of Fraction 2-3, and the freezing points of the fractions.

TABLE 3

| Fraction No. | HTM, ° C. | Amount, % | Freezing point, ° C. |
|---|---|---|---|
| 2-4 | 109.5 | 14.6 | 108.90 |
| 2-5 | 111.4 | 21.7 | 109.10 |
| 2-6 | 130 | 63.7 | 109.47 |

The results in Table 3 show that the purity of Fraction 2-3 can be further enhanced by another melt crystallization. The composition of Fraction 2-6 was analyzed and it was found to contain 0.08% wt of the monomethyl ester of 2,5-FDCA, based on the weight of Fraction 2-6. No other impurities could be detected, indicating the removal of coloration-causing compounds. The balance of the fraction was dimethyl-2,5-furandicarboxylate.

COMPARATIVE EXAMPLE 3

In this comparative example it is shown that melt crystallization is unsuitable for purifying crude ester compositions of dialkyl-2,5-furandicarboxylaye when such compositions contain more than 5% wt of the monoalkyl ester of 2,5-FDCA.

Fractions 1-1, 1-2 and 2-1 were combined. The mixture contained more than 7.5% wt of the monomethyl ester of 2,5-FDCA and more than 1500 ppmw of other impurities, the balance being dimethyl-2,5-furandicarboxylate.

The mixture was subjected to melt crystallization, following in general the procedure as outlined in Example 1, but only one fraction was collected as sweat fraction. The results are shown in Table 4 below.

TABLE 4

| Fraction No. | HTM, ° C. | Amount, % | Freezing point, ° C. |
|---|---|---|---|
| 3-1 | 104 | 6.2 | 104.3 |
| 3-2 | 110 | 13.8 | 104.7 |
| 3-3 | 130 | 80.0 | 104.9 |

The results in Table 4 show that hardly any increase in freezing point can be achieved by melt crystallizing the dimethyl ester composition that contained more than 7.5% wt of the monomethyl ester. The level of contaminants in Fraction 3-3 was still more than 1350 ppmw.

The invention claimed is:

1. A process for purifying an ester composition comprising at least 90% wt of the dialkyl ester of 2,5-furandicarboxylic acid as starting dialkyl ester concentration and up to 5% wt of the monoalkyl ester of 2,5-furandicarboxylic acid as starting monoalkyl ester concentration, the percentages being based on the weight of the ester composition, which process comprises subjecting the ester composition to melt crystallization to yield a purified dialkyl ester composition containing a dialkyl concentration higher than the starting dialkyl ester concentration and a melt residue containing a monoalkyl ester concentration higher than the starting monoalkyl ester concentration,
wherein the melt residue is subject to conversion into a monoalkyl ester-rich intermediate product containing a momoalkyl ester concentration of at least 10% wt, based on the weight of the intermediate product, and
wherein the monoalkyl ester-rich intermediate product that is subjected to melt crystallization has a temperature in the range of 180 to 250° C.

2. The process according to claim 1, wherein the ester composition comprises up to 10% wt of contaminants.

3. The process according to claim 2, wherein the contaminants include one or more compounds selected from the group consisting of 5-formyl-furan-2-carboxylic acid, an alkyl ester of 5-formyl-furan-2-carboxylic acid, 2,5-furandicarboxylic acid and coloration-causing compounds.

4. The process according to any one of claim 1, wherein the melt crystallization of the ester composition is conducted in a static, falling film and/or suspension melt crystallization equipment.

5. The process according to claim 4, wherein the melt crystallization of the ester composition is conducted in a static or falling film melt crystallization equipment, wherein crystallization takes place on cooled surfaces.

6. The process according to claim 5, wherein melt crystallization is conducted in a falling film equipment, wherein the molten ester composition is passed along the walls of cooling tubes as cooled surfaces to effect crystallization of the dialkyl ester of 2,5-furandicarboxylic acid on the walls of the cooling tubes.

7. The process according to claim 5, wherein, after the crystallization of the dialkyl ester of 2,5-furandicarboxylic acid on the cooled surfaces, the cooled surfaces are re-heated to a temperature below the melting point of the dialkyl ester of 2,5-furandicarboxylic acid, to effect the melting of low-melting components that are obtained as sweat, in addition to the purified dialkyl ester composition and the melt residue.

8. The process according to claim 1, wherein the ester composition being subjected to melt crystallization has a temperature in the range of 110 to 200° C.

9. The process according to claim 1, wherein the conversion of the melt residue is a transesterification of the dialkyl ester with 2,5-furandicarboxylic acid.

10. The process according to claim 1, wherein the conversion of the melt residue is partial hydrolysis.

11. The process according to claim 1, wherein the melt residue is subjected to evaporation to vaporize the dialkyl ester of 2,5-furandicarboxylic acid and recover the remaining liquid as monoalkyl ester-rich intermediate product.

12. The process according to claim 1, wherein the monoalkyl ester-rich intermediate product is subjected to melt crystallization to yield a purified monoalkyl ester composition and a contaminants-rich residue.

13. The process according to claim 1, wherein the melt crystallization of the monoalkyl ester-rich intermediate product is conducted in a static, falling film and/or suspension melt crystallization equipment.

14. The process according to claim 1, wherein the ester composition has been obtained in a process, comprising:
contacting a vaporous stream of an alkanol counter-currently with a liquid starting material comprising 2,5-furandicarboxylic acid in a reaction zone to conduct an esterification reaction to a dialkyl ester of 2,5-furandicarboxylic acid and water;
withdrawing a reaction vapor comprising the alkanol and water from the reaction zone; and
discharging a liquid phase comprising at least the dialkyl ester of 2,5-furandicarboxylic acid, from the bottom part of the reaction zone, to obtain the ester composition comprising the dialkyl ester of 2,5-furandicarboxylic acid.

15. The process according to claim 14, wherein the liquid phase obtained in the esterification reaction is separated into a first fraction rich in the monoalkyl ester of 2,5-furandicarboxylic acid and a second fraction rich in the dialkyl ester of 2,5-furandicarboxylic acid, said second fraction being subjected to melt crystallization as the ester composition.

16. The process for the preparation of 2,5-furandicarboxylic acid from an ester composition comprising at least 90% wt of the dialkyl ester of 2,5-furandicarboxylic acid as starting dialkyl ester concentration and up to 5% wt of the monoalkyl ester of 2,5-furandicarboxylic acid as starting monoalkyl ester concentration, the percentages being based on the weight of the ester composition, comprising
purifying the ester composition in a process according to claim 1, to yield a purified dialkyl ester composition containing a dialkyl ester concentration higher than the starting dialkyl ester concentration and a melt residue containing a monoalkyl ester concentration higher than the starting monoalkyl ester concentration; and hydrolysing the purified dialkyl ester composition to yield purified 2,5-furandicarboxylic acid.

17. The process according to claim 16, which further comprises:

subjecting the melt residue to conversion into a monoalkyl ester-rich intermediate product containing a monoalkyl ester concentration of at least 10% wt, based on the weight of the intermediate product;

subjecting the monoalkyl ester-rich intermediate product to melt crystallization to yield a purified monoalkyl ester composition; and hydrolysing the purified monoalkyl ester composition to yield purified 2,5-furandicarboxylic acid.

18. The process according to claim 16, wherein purified dialkyl ester composition and purified monoalkyl ester composition are combined and hydrolysed simultaneously.

\* \* \* \* \*